United States Patent
Highsmith et al.

(10) Patent No.: US 10,285,751 B2
(45) Date of Patent: May 14, 2019

(54) SYSTEM AND METHOD FOR CONTROLLING CATHETER POWER BASED ON RENAL ABLATION RESPONSE

(71) Applicant: BIOSENSE WEBSTER (ISRAEL) LTD., Yokneam (IL)

(72) Inventors: Debby E. Highsmith, Laguna Niguel, CA (US); Eduardo Jimenez, Fullerton, CA (US); Kristine B. Fuimaono, Costa Mesa, CA (US)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 746 days.

(21) Appl. No.: 14/885,816

(22) Filed: Oct. 16, 2015

(65) Prior Publication Data

US 2017/0105783 A1 Apr. 20, 2017

(51) Int. Cl.
*A61B 18/12* (2006.01)
*A61B 18/14* (2006.01)
(Continued)

(52) U.S. Cl.
CPC ...... *A61B 18/1233* (2013.01); *A61B 18/1492* (2013.01); *A61B 34/25* (2016.02);
(Continued)

(58) Field of Classification Search
CPC . A61B 18/1492; A61B 18/14; A61B 18/1233; A61B 2018/124; A61B 2018/1467; A61B 2018/00577; A61B 2018/00511; A61B 2018/00779; A61B 2018/00791; A61B 2018/00875;
(Continued)

(56) References Cited

U.S. PATENT DOCUMENTS 6,063,078 A * 5/2000 Wittkampf ......... A61B 18/1492
606/41
6,425,894 B1 7/2002 Brucker et al.
(Continued)

OTHER PUBLICATIONS

Extended European Search Report for European Application No. EP16193861, dated Mar. 28, 2017, 5 pages.

*Primary Examiner* — Thomas A Giuliani
(74) *Attorney, Agent, or Firm* — Roberts Mlotkowski Safran Cole & Calderon, P.C.

(57) ABSTRACT

An ablation system observes and monitors ablation parameters, including temperature, impedance, and/or the system's own closed-loop response to these ablation parameters. The system comprises a catheter with electrodes and a detection circuitry configured to detect an ablation parameter for each electrode, a controller coupled to the catheter, the controller having a processing unit and a memory storing instructions that, when executed by the processing unit, cause the processing unit to: receive a detected ablation parameter for each electrode from the detection circuitry, determine when a detected ablation parameter violates a defined ablation parameter for each electrode, control a power supplied to each violating electrode to have a reduced power, detect a rate of power reduction for each violating electrode, and stop the power supplied to each violating electrode when a respective detected rate of power reduction exceeds a threshold rate of power reduction.

11 Claims, 9 Drawing Sheets

(51) Int. Cl.
*A61B 34/00* (2016.01)
*A61B 18/00* (2006.01)

(52) U.S. Cl.
CPC ............... *A61B 2018/00434* (2013.01); *A61B 2018/00511* (2013.01); *A61B 2018/00577* (2013.01); *A61B 2018/00648* (2013.01); *A61B 2018/00654* (2013.01); *A61B 2018/00672* (2013.01); *A61B 2018/00678* (2013.01); *A61B 2018/00708* (2013.01); *A61B 2018/00779* (2013.01); *A61B 2018/00791* (2013.01); *A61B 2018/00821* (2013.01); *A61B 2018/00875* (2013.01); *A61B 2018/00886* (2013.01); *A61B 2018/00898* (2013.01); *A61B 2018/1467* (2013.01)

(58) Field of Classification Search
CPC ........... A61B 2018/00434; A61B 2018/00898; A61B 2018/00636; A61B 2018/00642; A61B 2018/00648; A61B 2018/00654; A61B 2018/00666; A61B 2018/00702; A61B 2018/00708; A61B 2018/00714; A61B 2018/00755; A61B 2018/00678; A61B 2018/00672

USPC ......................................... 606/34, 38, 41, 42
See application file for complete search history.

(56) References Cited

U.S. PATENT DOCUMENTS

| | | |
|---|---|---|
| 7,536,218 B2 | 5/2009 | Govari et al. |
| 8,478,383 B2 | 7/2013 | Bar-Tal et al. |
| 8,623,007 B2 | 1/2014 | Deborski et al. |
| 9,855,094 B2 * | 1/2018 | Christian ........... A61B 18/1492 |
| 2005/0177053 A1 | 8/2005 | Boveja et al. |
| 2008/0255642 A1 * | 10/2008 | Zarins ................ A61B 18/1206 607/99 |
| 2012/0136350 A1 | 5/2012 | Goshgarian et al. |
| 2012/0265198 A1 | 10/2012 | Crow et al. |
| 2013/0296850 A1 | 11/2013 | Olson |
| 2014/0018788 A1 | 1/2014 | Engelman et al. |
| 2014/0163543 A1 | 6/2014 | Allison et al. |
| 2014/0276766 A1 | 9/2014 | Brotz et al. |

* cited by examiner

SYSTEM AND METHOD FOR CONTROLLING CATHETER POWER BASED ON RENAL ABLATION RESPONSE

FIELD OF INVENTION

Aspects of embodiments of the present invention relate to invasive medical devices and associated control systems capable of ablation and sensing ablation responses, such as a catheter, and control systems capable of adjusting the power supplied to the catheter based on the sensed responses.

BACKGROUND OF INVENTION

Catheterization is used in diagnostic and therapeutic procedures. For example, a cardiac catheter is used for mapping and ablation in the heart to treat a variety of cardiac ailments, including cardiac arrhythmias, such as atrial flutter and atrial fibrillation which persist as common and dangerous medical ailments, especially in the aging population. Diagnosis and treatment of cardiac arrhythmias include mapping the electrical properties of heart tissue, especially the endocardium and the heart volume, and selectively ablating cardiac tissue by application of energy. Such ablation can cease or modify the propagation of unwanted electrical signals from one portion of the heart to another. The ablation process destroys the unwanted electrical pathways by formation of non-conducting lesions. Various energy delivery modalities have been disclosed for forming lesions, and include use of microwave, laser and more commonly, radiofrequency energies to create conduction blocks along the cardiac tissue wall. In a two-step procedure—mapping followed by ablation—electrical activity at points within the heart is typically sensed and measured by advancing a catheter containing one or more electrical sensors (or electrodes) into the heart, and acquiring data at a multiplicity of points. These data are then utilized to select the endocardial target areas at which ablation is to be performed.

The term "radiofrequency" (RF) is commonly used to refer to an alternating current that flows through a conductor. In the case of ablation, RF current flows through biological tissue that contains free ions. The extra cellular fluid present in the tissue provides the electrical conductivity. The tissue conductivity can be represented by tissue impedance. In general, low impedance represents high conductivity and high impedance represents low conductivity.

The application of RF current biological tissue causes heating of tissue. The higher the RF current density in the biological tissue (current per unit area), the higher the resulting temperature. The tissue stops reacting to electrical stimulation when heated above a threshold over a short period.

Another catheter-based ablation procedure is renal denervation (RDN). It is a minimally invasive, endovascular catheter based procedure using radiofrequency ablation aimed at treating medical conditions and diseases, including, for example, hypertension. The sympathetic system fuels the release of certain hormones that affect and control blood pressure. In hypertension, the continued release of low-dose amounts of these hormones can increase blood pressure. Hypertension can be controlled by diet, exercise and drugs. However, resistant hypertension (commonly defined as blood pressure that remains above goal in spite of concurrent use of three antihypertensive agents of different classes) requires more aggressive treatments, including surgery. Resistant hypertension is a common clinical problem faced by both primary care clinicians and specialists. As older age and obesity are two of the strongest risk factors for uncontrolled hypertension, the incidence of resistant hypertension will likely increase as the population becomes more elderly and heavier.

It has been established that severing the renal nerves improves blood pressure. However, this procedure involves surgery and all its attendant risks, and often resulted in global sympathetic denervation below the chest. Being able to de-nervate, or silence, only the renal nerves through a catheter-based system is a crucial development. A small catheter is placed in the femoral artery and access to the nerves is gained through the renal artery. The nerves are woven and embedded in the casings or layers around the renal arteries. By passing an energy source into the renal artery and transmitting a low-dose energy, radiofrequency ablation, through the catheter, inbound and exiting renal sympathetic nerves are exposed to RF current densities. The extent of heating is proportional to the RF power (current density) output. At low current densities, the tissue is heated slowly and contracts because of fluid loss. With the nerves impaired or "denerved" at selected locations along their lengths, sympathetic afferent and efferent activity is interrupted or reduced with beneficial effects, such as a reduction in blood pressure.

Current ablation systems provide electrophysiologist with temperature, impedance and power feedback during an ablation procedure. However, unlike cardiac ablation, such feedback in renal ablation denervation does not readily provide information on acute end point indicating successful ablation. That is, such feedback information does not readily help determine whether renal nerves have been impacted by the ablation. However, renal arteries can be prone to exhibit physiological response during ablation. One response includes the potential for arterial spasming.

During spasming, an artery can suddenly narrow, constricting blood flow through the artery. With a reduced inner diameter, the artery can close in on the ablating electrode, increasing the surface area of the artery in contact with the electrode and hence improving ablation efficiency by increasing the amount of ablation power delivered to the tissue. However, with the increasing amount of ablation power, there is a greater risk for artery stenosis. Renal artery stenosis is undesirable, if not dangerous, because narrowing of the renal arteries prevents normal amounts of oxygen-rich blood from reaching the kidneys which need adequate blood flow to help filter waste products and remove excess fluids. Reduced blood flow may increase blood pressure and injure kidney tissue.

Accordingly, there is a desire for a system and a method of renal arterial ablation which help monitor the potential for renal arterial spasming as an indicator of ablation while controlling the amount of ablation power applied to reduce the risk of undesirable damage to the renal artery as a result of excessive ablation.

SUMMARY OF THE INVENTION

The present invention is directed to an ablation system which observes and monitors ablation parameters, including temperature, impedance, and/or the system's own closed-loop response to these ablation parameters in delivery of power to one or more ablation electrodes, including cessation of power delivery to one or more electrodes while maintaining power delivery to one or more other electrodes.

In some embodiments, system comprises a catheter with one or more electrodes and a detection circuitry configured to detect an ablation parameter for each electrode; a controller coupled to the catheter, the controller having a processing unit and a memory storing instructions that, when executed by the processing unit, cause the processing unit to: receive a detected ablation parameter for each electrode from the detection circuitry, control a power supplied to each violating electrode to have a reduced power when the respective detected ablation parameter violates a defined ablation parameter, detect a rate of power reduction for each violating electrode, and stop the power supplied to each violating electrode when a respective detected rate of power reduction exceeds a threshold rate of power reduction.

In some detailed embodiments, the detected ablation parameter is temperature or impedance, and the defined ablation parameter includes a user defined ablation parameter or a system-defined ablation parameter.

In some detailed embodiments, the memory further stores instructions that, when executed by the processing unit, cause the processing unit to control the power supplied to each violating electrode in accordance with a power control curve.

In some detailed embodiments, the power control curve includes a piecewise continuous function.

In some embodiments, the memory further stores instructions that, when executed by the processing unit, cause the processing unit to stop the power supplied to each electrode when an ablation session time exceeds a threshold ablation session time.

In some embodiments, the defined ablation parameter includes a user-defined ablation parameter, wherein the memory further stores instructions that, when executed by the processing unit, cause the processing unit to reject the user-defined ablation parameter when the user-defined ablation parameter violates a system-defined ablation parameter.

In some embodiments, the user-defined ablation parameter is selected from the group consisting of maximum threshold temperature, and minimum threshold temperature, and the system-defined ablation parameter is selected from the group consisting of maximum system temperature, and threshold increase of detected temperature above the maximum threshold temperature at which the power to each violating electrode is reduced.

In some embodiments, the user-defined ablation parameter is selected from the group consisting of maximum threshold impedance, and minimum threshold impedance, and the system-defined ablation parameter is selected from the group consisting of maximum system impedance and minimum system impedance.

In other embodiments, a renal ablation system, comprises a catheter comprising one or more electrodes and a temperature sensing circuitry configured to sense a temperature for each electrode; a controller coupled to the catheter, the controller comprising a processing unit and a memory storing instructions that, when executed by the processing unit, cause the processing unit to: receive a detected temperature for each electrode from the temperature sensing circuitry, control a power supplied to a violating electrode to have a reduced power level when the detected temperature of the violating electrode is greater than a threshold temperature, receive a detected rate of power reduction of the violating electrode, and stop the power supplied to the violating electrode when the detected rate of power reduction of the violating electrode exceeds a threshold rate of power reduction.

In other embodiments, a renal ablation system comprises a catheter comprising one or more electrodes and a temperature sensing circuitry configured to sense a temperature for each electrode, a controller coupled to the catheter, the controller comprising a processing unit and a memory storing instructions that, when executed by the processing unit, cause the processing unit to: receive a first detected temperature for each electrode from the temperature sensing circuitry, control a power supplied to a violating electrode to have a reduced power level when the detected temperature of the violating electrode is greater than a threshold temperature, receive a subsequent detected temperature for the violating electrode following a reduction of power level supplied to the violating electrode, and stop the power supplied to the violating electrode when the subsequent detected temperature is not equal to or lower than the threshold temperature.

The present invention is also directed to methods for ablating. In some embodiments, a method for ablating comprises: receiving a detected temperature for each electrode from the temperature sensing circuitry, controlling a power supplied to a violating electrode to have a reduced power level when the detected temperature of the violating electrode is greater than a threshold temperature, receiving a detected rate of power reduction of the violating electrode, and stopping the power supplied to the violating electrode when the detected rate of power reduction of the violating electrode exceeds a threshold rate of power reduction.

In other embodiments, the method comprises: receiving a first detected temperature for each electrode from the temperature sensing circuitry, controlling a power supplied to a violating electrode to have a reduced power level when the detected temperature of the violating electrode is greater than a threshold temperature, receiving a subsequent detected temperature for the violating electrode following a reduction of power level supplied to the violating electrode, and stopping the power supplied to the violating electrode when the subsequent detected temperature is not equal to or lower than the threshold temperature.

BRIEF DESCRIPTION OF THE DRAWINGS

These and other features and advantages of the present invention will be better understood by reference to the following detailed description when considered in conjunction with the accompanying drawings wherein.

DETAILED DESCRIPTION OF THE INVENTION

Figure 1:
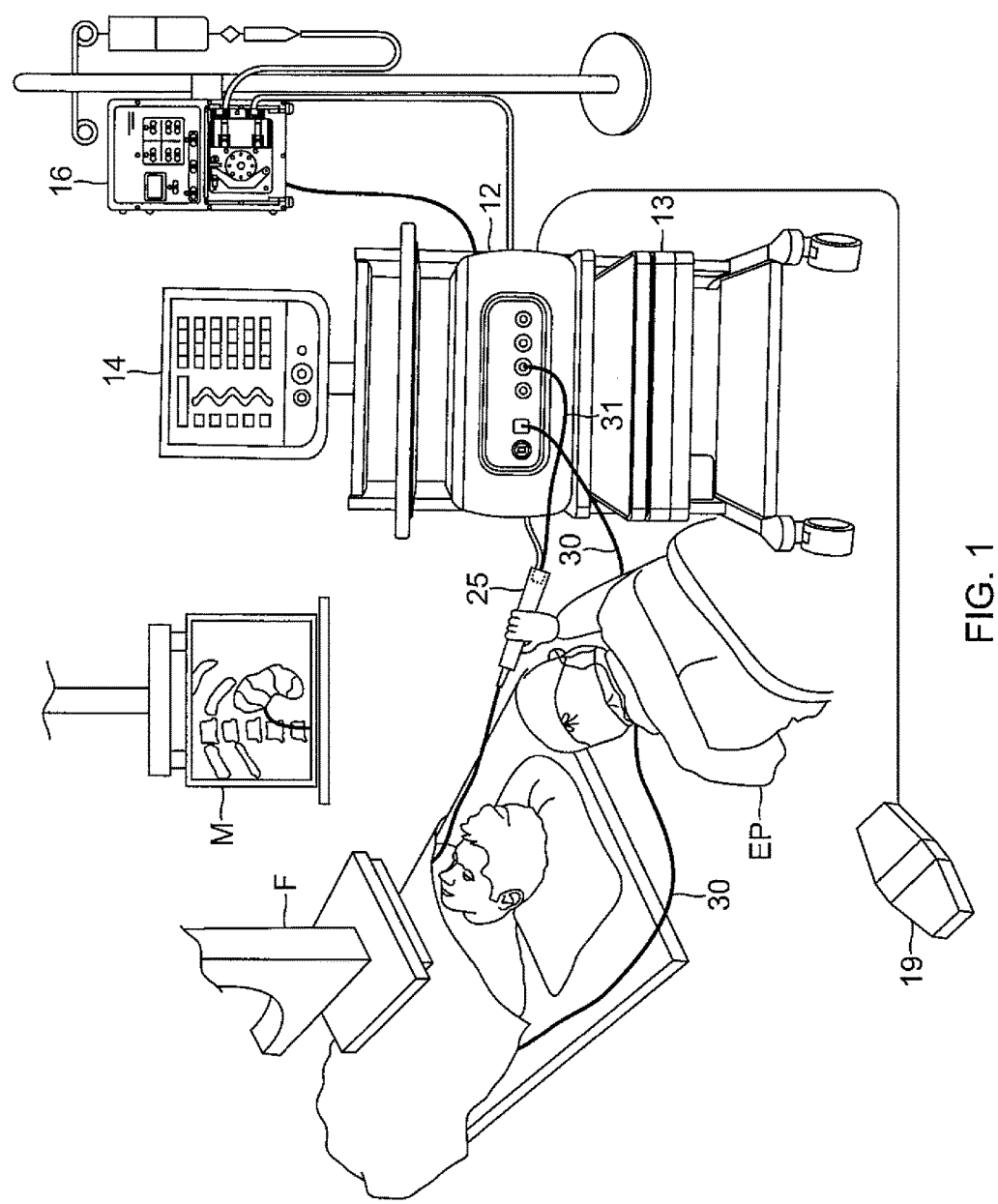
FIG. 1 is a schematic, pictorial illustration of a catheter-based ablation system, in accordance with an embodiment of the present invention.
Figure 2A:
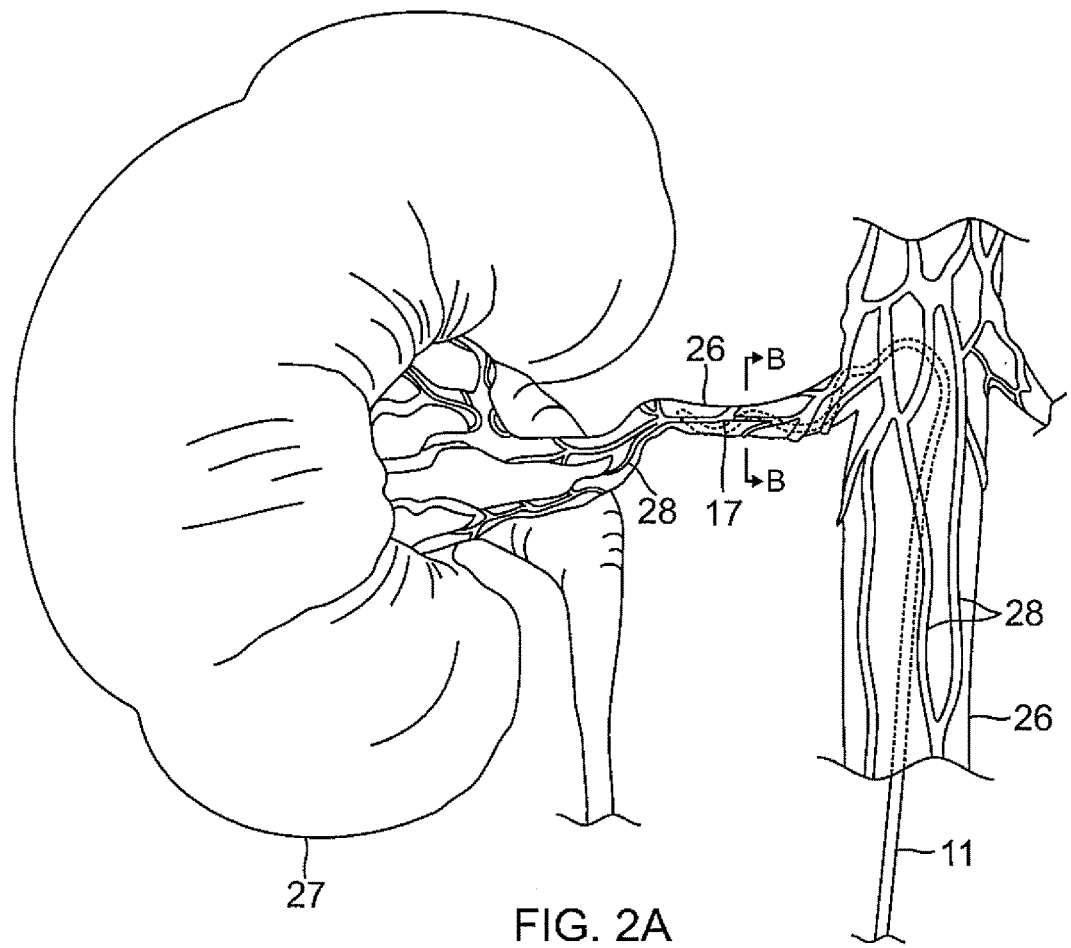
FIG. 2A is a schematic view of a renal artery with a catheter extending therethrough.
Figure 2B:
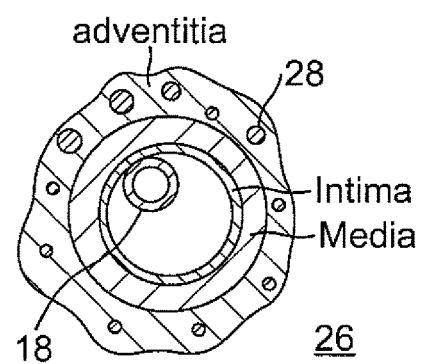
FIG. 2B is a cross-end sectional view of the renal artery and the catheter of FIG. 2A, taken along line B-B.
Figure 3:
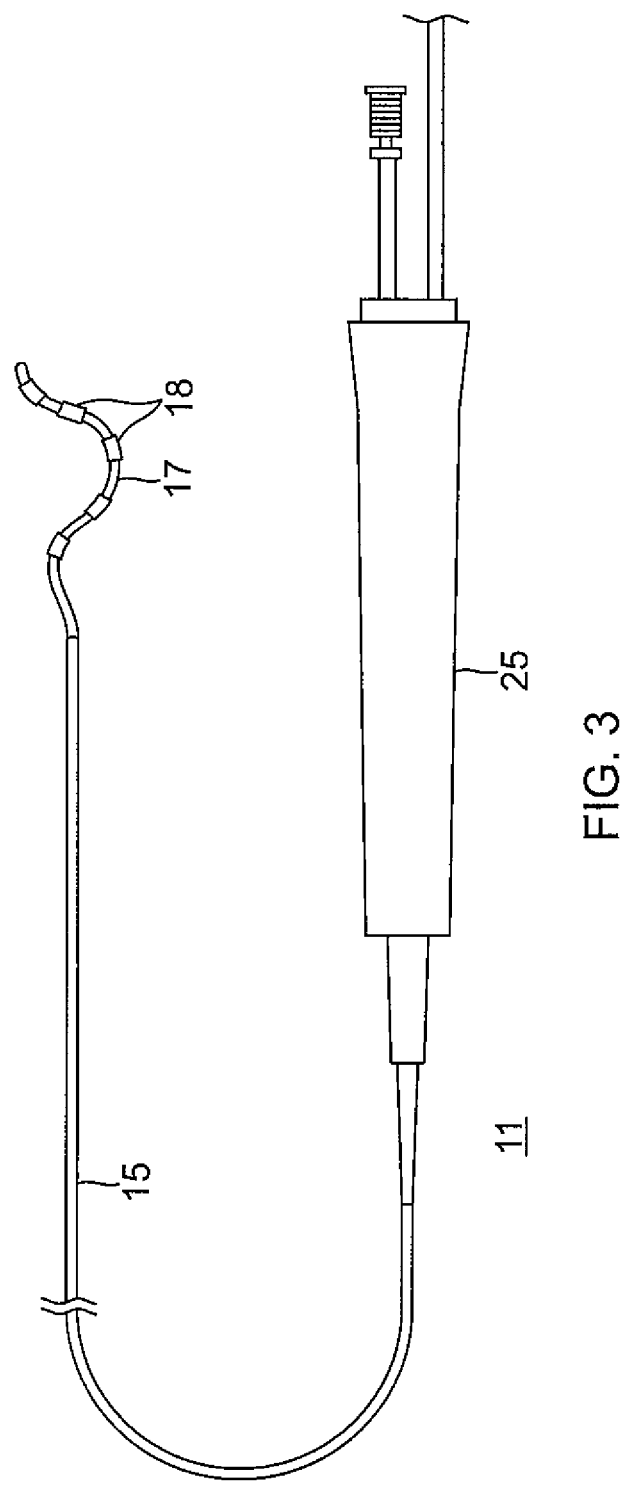
FIG. 3 is a side view of a catheter of the present invention, in accordance with one embodiment.

The present invention is directed to a catheter-based ablation system 10, with embodiments illustrated in FIG. 1, including a catheter 11, an RF generator console 12, a power supply 13, a display monitor 14, an irrigation pump 16, and an ablation actuator 19 (e.g., a foot pedal). The system 10 is adapted for renal ablation performed within a renal artery 26 near a kidney in denerving surrounding nerves 28, as shown in FIG. 2A and FIG. 2B. In some embodiments as shown in FIG. 3, the catheter 11 includes a control handle 25, a catheter body 15 and a helical distal portion 17 on which electrodes 18 are mounted, each adapted for contact with a different surface area of the inner circumferential tissue along the artery 26. As known in the art, the catheter enters the body of patient P via an opening in the femoral artery and is then advanced through the patient's vasculature by an electrophysiology professional EP under fluoroscopic guidance by means of a fluoroscope F and a monitor M, or other suitable guidance means, to position the helical distal portion 17 in the renal artery 26 in order to ablate renal plexus nerve fibers 28 located around the renal artery 26. The nerve fibers enter the kidney with the branches of the renal artery. In some embodiments, the catheter 11 has a plurality of five irrigated electrodes 18A-18E, although it is understood that the plurality may range between about three and eight.

Figure 4:
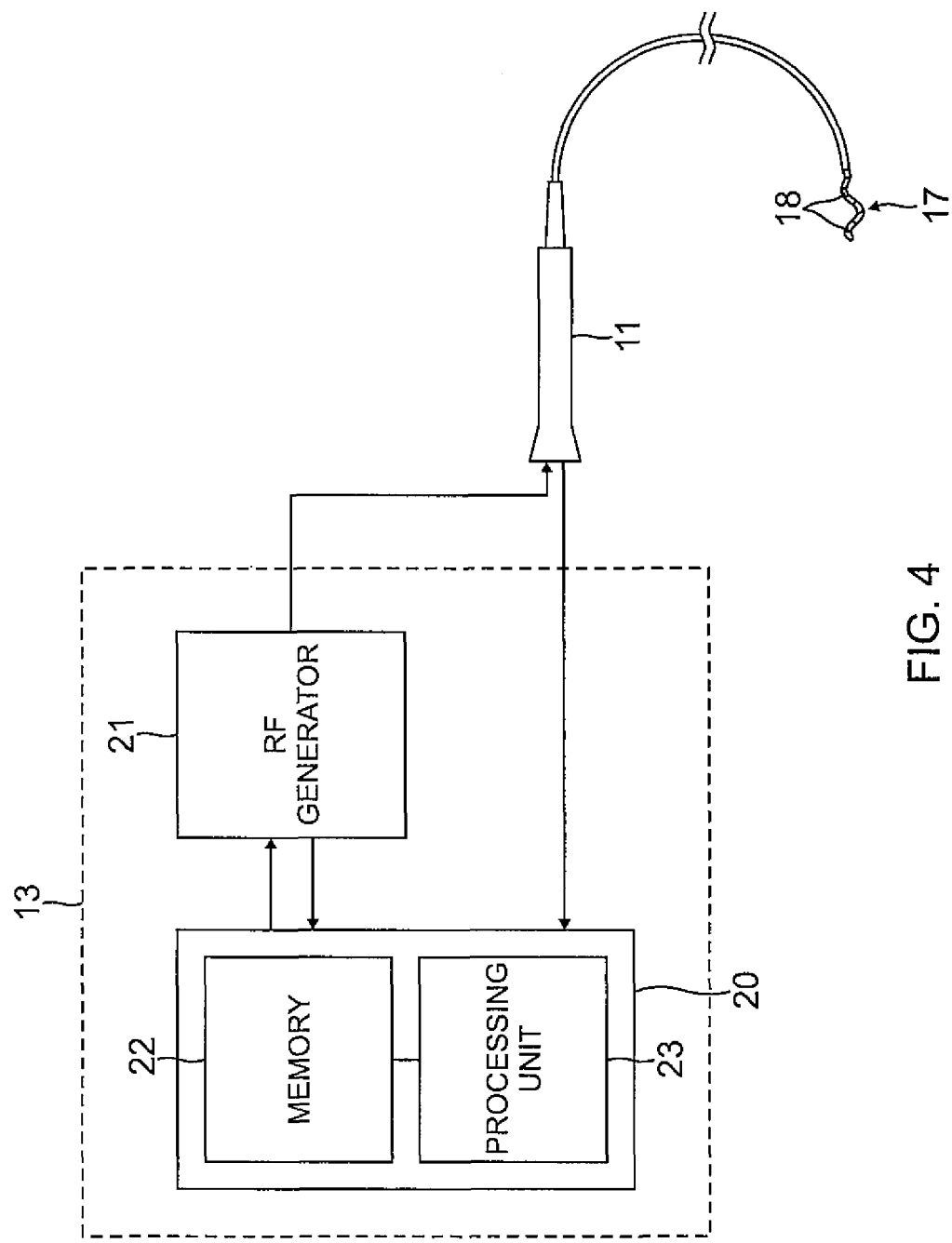
FIG. 4 is a schematic block diagram of a portion of the catheter-based ablation system of FIG. 1.

In some embodiments as shown in FIG. 4, the RF generator console 13 includes a controller 20 with memory 22 and processing unit 23, and an RF signal generator 21. The memory 22 stores instructions that, when executed by the processing unit 23, cause the controller 20 to control the RF power output by the RF signal generator 21 (e.g., by adjusting the output current) to the electrodes 18 on the catheter 11. The processing unit 23 may be any sort of computing device suitable for controlling the power output, for example, a general purpose processor coupled to a memory (e.g., dynamic random access memory and/or flash memory), a microcontroller, an appropriate programmed field programmable gate array (FPGA), or an application specific integrated circuit (ASIC).

The catheter 11 is configured with a plurality of diagnostic and therapeutic electrodes $18i$ adapted to ablate and also to provide signals, including signals representative of ablation electrode temperature and tissue impedance, which are received and processed by the controller 20. RF generator 21 actively generates RF energy and the controller 20 continuously monitors, displays, and coordinates ablation parameters, including, the amount of RF energy delivered to the catheter 11, the temperature of the catheter ablation electrodes 18, and the tissue impedance during ablation therapy. The temperature of each ablation electrode is measured for each electrode, for example, by a respective sensor or a thermal monitoring circuit, as described in U.S. Pat. No. 6,425,894. Simultaneously, tissue impedance is measured at each electrode allowing detection of small tissue changes before, during, and after treatment. Advantageously, "measured ablation parameters" (MAP) including temperature and impedance as sensed by the catheter 11 and measured by the processing unit 23 are monitored in real time by the controller 20 to provide "closed loop" feedbacks for controlling and adjusting ablation output power.

Figure 5:
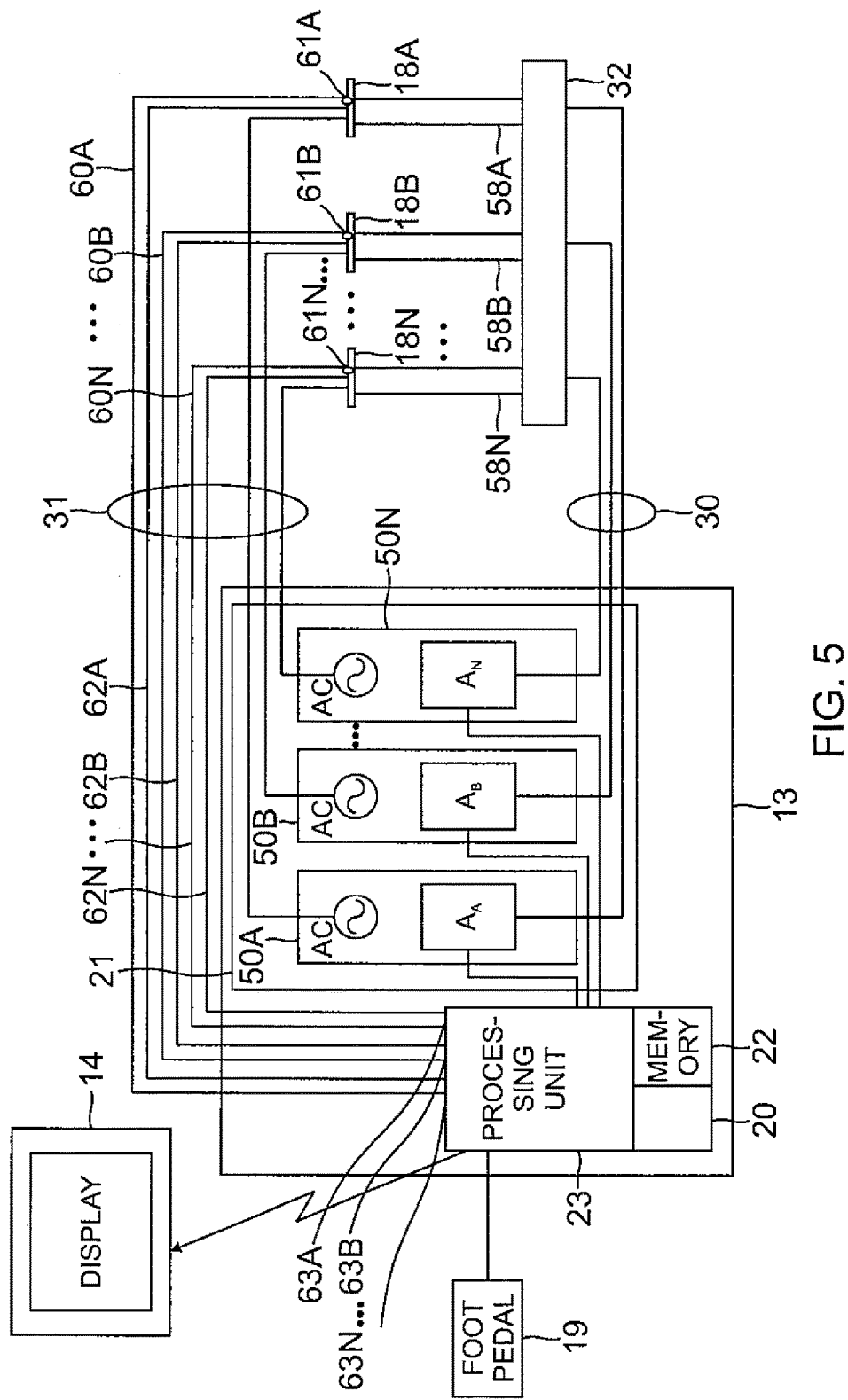
FIG. 5 is a schematic block diagram of circuitry used in the catheter-based ablation system of FIG. 1, in accordance with one embodiment.

FIG. 5 is a block diagram showing elements of system 10 and illustrating the flow of power and information, in accordance with some embodiments. The RF generator console 13 includes various circuitry, including circuitry for driving currents, for measuring impedance and for measuring temperature.

In some embodiments, the system 10 is configured to perform unipolar ablation with RF current along a closed circuit for each electrode. The RF current flows from the RF generator console 13 to each of the electrodes 18 via an electrical connection (e.g., cable 31, see FIG. 1) to the catheter 11. The current passes through patient tissue and back to the RF generator console 13 through an indifferent electrode 32 (e.g., a body surface patch) which is connected to the console 13 via an electrical connection (e.g., cable 30, see FIG. 1). The indifferent electrode 32 may be affixed to the back of the patient's body, near the target kidney region. In order for the tissue heating to occur at only the interface between the selected ablation electrode(s) and the tissue, the indifferent electrode 32 should have a considerably larger surface area than the ablation electrode(s). Because the current density is highest at the ablation electrode(s), most of the RF energy is converted into heat in the area of the ablation electrode(s).

For N plurality of electrodes on the catheter, each of N circuits 50A, 50B, . . . , 50N drives a current through a closed loop consisting of a catheter electrode $18i$ and the indifferent electrode 32. In some embodiments, each circuit $50i$ drives a current through body tissue $58i$, which lies between electrode $18i$ and the indifferent electrode 32. Each of the currents generated by the driver circuits with a voltage generator Ai may be distinguished by setting the circuits at different frequencies.

Each circuit $50i$ measures the electrical impedance in its respective loop through the body tissue. These impedance readings are passed to the processing unit 23, which uses the readings to adjust the power delivered to each electrode $18i$. In some embodiments, the circuits generate constant voltage signals. For a constant voltage, the impedance between the catheter electrode $18i$ and the patch electrode 32 in each closed loop $50i$ is inversely proportional to the current that flows through the circuit $50i$. The circuits 50A-50N measure the currents flowing through the respective loops to determine impedances. In other embodiments, circuits 50A-50N generate constant current signals. For a constant current, the impedance between the electrode $18i$ and the patch electrode 32 in each closed loop is proportional to the voltage between the two. Measurement of the voltage across the current drivers can therefore be measured by the RF generator to determine impedances.

In any of embodiments described above, the impedance measured for any pair of an electrode $18i$ and the patch electrode 32 is proportional to the distance between them. These distances may then be used for other purposes, including triangulation of the position at the tip of catheter 11.

Figure 6A:
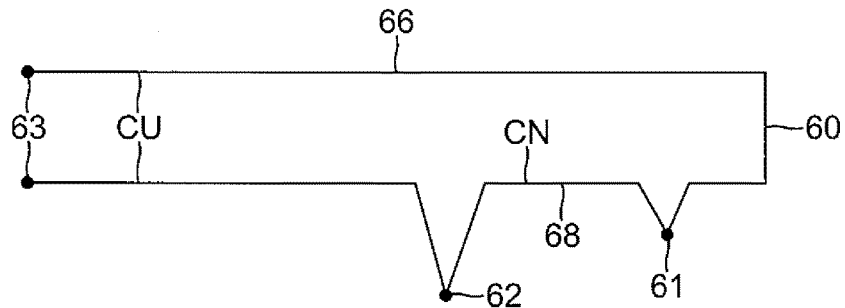
FIG. 6A is a schematic circuit diagram of a thermocouple.

The RF generator console 13 also includes a temperature sensing circuitry, e.g., a thermocouple $60i$, for each electrode $18i$. These temperature readings are passed to the processing unit 23, which uses the readings to adjust the power delivered to each electrode 18*i*. In some embodiments, the temperature of each electrode is monitored by a pair of conductive wires to relay information from the sensor. As known in the art, a thermocouple operates on the thermoelectric principle that when two dissimilar metals are joined together, an electrical voltage is generated which is proportional to the metal composition and junction temperature (Seebeck effect). As shown in FIG. 6A, a thermocouple 60 is typically comprised of a sensing junction 61 and a reference junction 62 and a terminal 63 formed and connected by thermocouple wire pair 66 and 68, for example, a copper and a constantan wire. The reference junction 62 and the sensing junction 61 produce DC voltages having opposite polarities and in proportion to the temperature at each junction. Consequently, where there is a difference in temperature between the sensing junction and the reference junction, a DC voltage is produced at the terminal 63. Where there is no difference in temperature between the sensing junction 61 and the reference junction 62, the voltages from the reference junction and the sensing junction cancel each other out and there is no voltage across the terminal 63.

Accordingly, as shown in FIG. 5, each electrode 18*i* has a thermocouple wire pair 60*i* with a sensing junction 61*i* in contact with or near the respective electrode 18*i*, a reference junction 62*i* in contact with a body providing a reference temperature, and a terminal 63*i* providing signal to the processing unit for determining and monitoring temperature of each electrode.

Figure 6B:
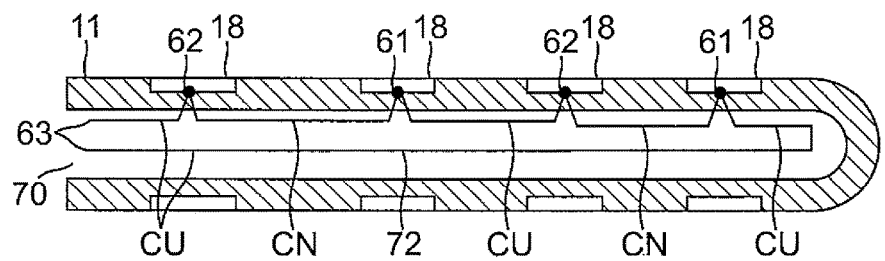
FIG. 6B is a diagrammatic side sectional view of a distal section of the catheter of FIG. 3, employing a thermal monitoring circuit in accordance with one embodiment.
Figure 6C:
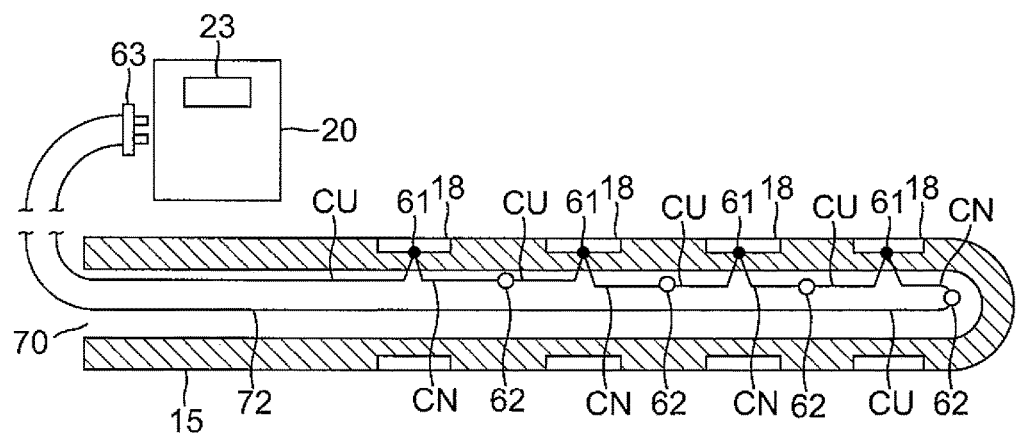
FIG. 6C is a diagrammatic side sectional view of a distal section of the catheter of FIG. 3, employing a thermal monitoring circuit in accordance with another embodiment.

In other embodiments as shown in FIG. 6B and FIG. 6C, the RF generator console 13 includes a thermal monitoring circuit 72 comprising a plurality of thermocouples connected in series configured to generate a voltage at a terminal 63 equal to the sum of the voltages generated by each thermocouple. The thermal monitoring circuit uses only two wires to travel through the elongated catheter body in order to monitor a plurality of electrodes.

Referring to FIG. 6B, the thermocouples 60 of the thermal monitoring circuit 72 are connected in series with the sensing junction 61 and the reference junction 62 of each thermocouple thermoconductively coupled to different electrodes 18, for example, attached thereto. Once the elongated catheter body is inserted into the patient's body, both the reference junctions 62 and the sensing junctions 61 are kept at relatively the same temperature, namely, the patient's body temperature. Once an electrode 18 is activated, the heat from the electrode causes the reference 62 or sensing junction 61 thermoconductively coupled to the activated electrode to generate a voltage, either positive or negative. If only one electrode is activated, the voltage at the terminal 63 is generated by the activated electrode. The absolute value of this voltage is reflective of the temperature at the activated electrode, and a temperature for the activated electrode can be calculated therefrom.

Referring to FIG. 6C, in an alternative embodiment of the thermal monitoring circuit 72 a portion the thermocouple junctions is attached to an electrode 18 while the other portion is thermally isolated from the electrode 18. This arrangement can be achieved by thermoconductively coupling the sensing junctions 61 to the electrodes 18 and thermally isolating the reference junctions 62 from the electrodes. In this configuration, a baseline voltage is generated at the terminal 63 due to the patient's body heat. Where only one electrode 18 is activated, an additional voltage at the terminal 63 is generated by the activated electrode, and a temperature for the activated electrode can be calculated therefrom. Where all the electrodes are activated in unison, an additional voltage attributable to the activated electrodes is generated at the terminal 63. An average temperature for each electrode can be calculated therefrom by dividing the additional voltage by the number of electrodes and calculating the average electrode temperature therefrom.

One way of thermally isolating the reference junctions 62 from the electrodes is by disposing the reference junctions 62 in a central lumen 70 in the elongated catheter body 15. By disposing the reference junctions 62 in the central lumen 70, the reference junctions 62 can be placed in the path of the irrigation flow which runs through the catheter. The irrigation flow can provide a relatively stable reference temperature. The reference junctions 62 can also be thermally isolated from the electrodes, by thermally sealing and insulating the reference junction 62 from the catheter environment.

Referring to both FIG. 6B and FIG. 6C, a plurality of thermocouples connected in series generates a voltage at the terminal 63 equal to the sum of the voltages generated by each thermocouple. Suitable thermal monitoring circuits are described in U.S. Pat. No. 6,425,894, the entire contents of which are incorporated herein by reference.

The system may also include catheter localization capabilities according to other embodiments of the present invention. A magnetic field is generated around the patient, for example, by a location pad (not shown) containing magnetic field generator coils that is placed under the patient. The magnetic fields generated by coils generate electrical signals in coils of an electromagnetic (EM) sensor located in the distal tip of catheter. The electrical signals are conveyed to a console which includes a processor or "workstation" that analyzes the signals so as to determine the coordinates of the position and orientation of catheter. The system may also be adapted for use with nonsensing catheters by providing hybrid magnetic-based and impedance positioning sensing capabilities, as described in U.S. Pat. No. 7,536,218 and U.S. Pat. No. 8,478,383 the entire contents of which are incorporated herein by reference. However, embodiments of the present invention are not limited thereto and may be used in systems without localization capabilities.

Being coupled (or connected) to the catheter 11, the RF generator console 13, as shown in FIG. 5, enables the operator to observe and regulate the functions of the catheter. The controller 20 of the console 13 drives the display monitor 14, for example, with touch screen capabilities to display a screen as a user interface for displaying information and receiving inputs from the operator.

It is understood that electrode temperature and impedance as measured by the system 10 can vary with certain limits during the course of a safe and successful ablation. Smaller temperature and impedance variations and fluctuations are generally acceptable as they typically result from normal tissue variances and/or signal processing (including noise) within the system. However, the system 12 recognizes that greater variances in electrode temperature and/or impedance may indicate excessive electrode heating which can cause undesirable tissue damage and/or reduce the effectiveness of ablating electrodes. Accordingly, the controller 20 is advantageously adapted to control the amount of RF energy (or power) the RF signal generator 21 supplies to the catheter based on defined ablation parameters (DAPs) and their relationship and correlation with measured (or determined, used interchangeably herein) ablation parameters (MAPs) based on temperature, impedance and/or power. Defined ablation parameters (DAPs) include system-defined ablation parameters (SDAPs) which are preset or preloaded into the system, and user-defined ablation parameters (UDAPs) which are defined by the user prior to operation of the system.

By reducing power supplied to the one or more electrodes when one or more measured (or detected, used interchangeably herein) ablation parameters (MAPs) meet, exceed or otherwise violate one or more defined ablation parameters (DAPs), the system operates with safety measures. For example, when output power is reduced to maintain the measured electrode temperature at or below a threshold or maximum temperature, the system can avoid excessive heating of tissue which may result in coagulum formation, charring of the renal artery tissue and blood, and/or vaporization of interstitial and intracellular fluid. For example, when output power is reduced to maintain the measured impedance below a threshold or maximum impedance, the system can avoid the formation of char and coagulum on ablating electrodes which can result in decreased RF energy delivery and/or an embolic event.

In accordance with features of the present invention, the system 10 enables the operator to set the value of one or more UDAPs via the touch screen display monitor 14. The UDAPs may be stored in the memory 22 along with instructions and SDAPs by which the processing unit 23 executes or employs to reduce the power output to each electrode 18$i$. In some embodiments, DAPs include the parameters shown in Tables 1 and 2, with selected parameters being UDAPs (Table 1) and others being SDAPs (Table 2). It is understood that in other embodiments, some SDAPs may be UDAPs and vice versa, as desired or appropriate. Table 3 includes various MAPs, including electrode temperature, impedance and rate of output power reduction.

TABLE 1

| User-Defined Ablation Parameters (UDAPs) | Definition | Sample Values (approx.) |
|---|---|---|
| P(u-max) | maximum output power for each electrode | 12 W |
| Temp(u-max) | maximum threshold for measured temperature above which the controller reduces the output power to violating electrode(s) until measured temperature is below the maximum threshold | 40 C. |
| Time(u-max) | maximum amount of time allowed per ablation session | 30 secs |
| Imp(u-max) | maximum threshold for measured impedance above which the controller reduces the power output to violating electrode(s) until measured impedance is below the maximum threshold | 250 Ω |
| Imp(u-min) | minimum threshold for measured impedance below which the controller reduces output power to violating electrode(s) until the measured impedance is greater the minimum threshold | 50 Ω |
| W(u) | time window within which to determine change in measured impedance | 3.0 secs |
| ΔImp(u-max) | maximum threshold for change in measured impedance within time window W, above which the controller reduces output power to violating electrode(s) until the change in measured impedance is below the maximum threshold | 100 Ω |

TABLE 2

| System-Defined Ablation Parameters (SDAPs) | Definition | Sample Values (approx.) |
|---|---|---|
| P(s-max) | maximum output power above which the controller rejects user input of P(u-max) | 15 W |
| Temp(s-max) | maximum temperature above which the controller rejects user input of Temp(u-max) | 40 C. |
| ΔTemp(s) | increase of measured temperature above Temp(u-max) at which the controller reduces output power to offending electrode(s) | 1 C. |
| Imp(s-max) | maximum impedance above which the controller rejects user input of Imp(u-max) | 51-300 Ω |
| Imp(s-min) | minimum impedance below which the controller rejects user input of Imp(u-min) | 5-50 Ω |
| ΔP/ΔTime(s-max) | threshold rate of change of power reduction by controller above which the controller stops output power to violating electrode(s) for remainder of ablation session | 1-4 W/1 sec, preferably 3 W/1 sec |
| C(s-max) | maximum number allowed for power reduction due to failure of electrode temperature to decrease after power reduction, beyond which the controller stops output power to violating electrode(s) | 2 |

TABLE 3

| Measured/Determined Ablation Parameters (MAPs) | Definition |
|---|---|
| Temp(meas) | measured electrode temperature |
| Imp(meas) | measured impedance |
| ΔP/ΔTime | determined or calculated rate of output power reduction |

As shown in Table 2, the controller 20 confines one or more UDAPs to ranges and or values in accordance with one or more SDAPs, for example, maximum electrode temperatures, maximum and minimum impedances, and maximum output power. Moreover, by monitoring one or more MAPs in accordance with one or more UDAPs, the controller responds to violation of one or more UDAPs by implementing output power reduction in one or more predetermined manners according to instructions stored in the memory and executed by the controller, as discussed below in further detail.

Where ablation is conducted in a renal artery, excessive heating can also cause arterial spasm which if allowed to continue can lead to severe arterial damage, with a significant risk of permanent arterial damage. Recognizing that a mere reduction in the power supplied to the ablating electrodes without an immediate following temperature drop may not be a sufficient response to stopping arterial spasm, the system is configured to cease the supply of power altogether to one or more violating electrodes during an ablation session, while continuing to supply power to non-violating electrodes. Accordingly, the controller 20 is not only adapted to reduce output power, but also to stop output power to one or more catheter electrodes for the remainder of the ablation session, by monitoring temperature response to power drop and/or the manner by which the controller responds to temperature and/or impedance activities of the each electrode. In some embodiments, the controller monitors a rate of output power reduction in determining whether to stop output power, as discussed further below in detail.

Figure 7:
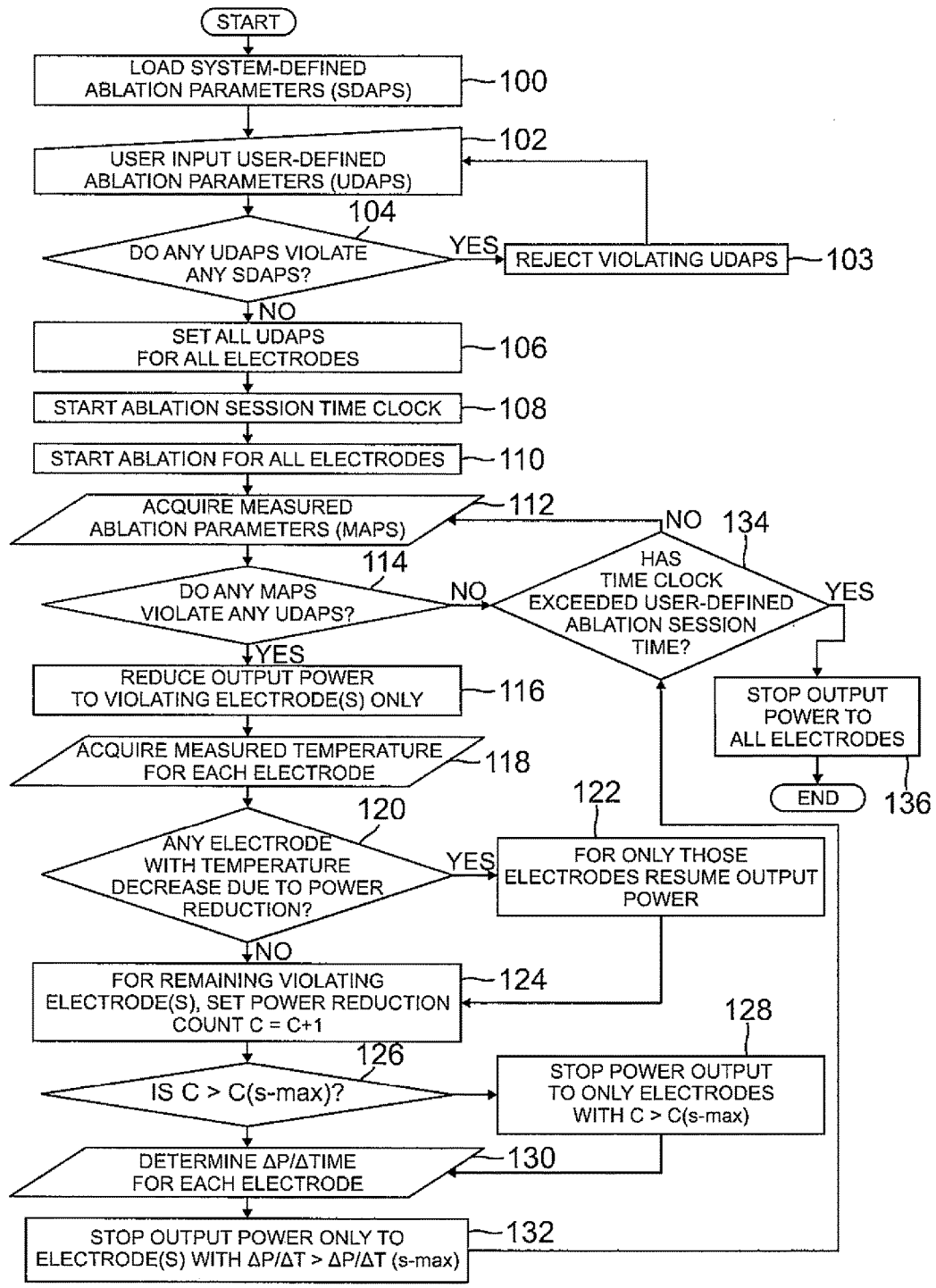
FIG. 7 is flowchart illustrating a method for controlling a power supplied to a catheter according to one embodiment of the present invention.

FIG. 7 is a flowchart illustrating a method 100 according to some embodiments of the present invention for the controller 20 to control the output power supplied to one or more electrodes of the catheter. In operation 100, after the operator has activated the system, the controller 20 retrieves from memory 23 the SDAPs and loads into the processing unit 23. In operation 102, the controller 20 queries operator to input UDAPs which are loaded into memory for retrieval and use by the processing unit 23. In operation 104, the processing unit compares and determines whether the UDAPs violate the SDAPs. If one or more UDAPs violate any of the SDAPs, the process turns to operation 103, wherein the violating UDAP(s) are rejected and the process returns to operation 102 which queries the operator for UDAPs. If no UDAPs violate any SDAPs, the process proceeds to operation 106 wherein the controller sets all UDAPS for each electrode, including the output power for each electrode, in compliance with the UDAPs and SDAPs.

In operation 108, the controller starts an ablation session time clock in compliance with the UDAP Time(max) to monitor the duration of the ablation session, and in operation 110, the controller commences the ablation session with the RF generator supplying output power in compliance with UDAP P(max) to each electrode.

In operation 112, the controller acquires MAPs in real time, for example, by measuring the temperature of each electrode Temp(meas) via the thermocouples 60$i$, the impedance of each electrode Imp(meas) via the circuits 50$i$, and determining the rate of power reduction ΔP/ΔTime implemented by the system in response to the measured temperatures Temp(meas) and/or the measured impedances Imp (meas).

In operation 114, the controller compares the DAPs with the UDAPs and determines whether there are any violating electrodes, for example, whether a measured temperature Temp (meas) of any electrode has exceeded the UDAP Temp (max) and/or a measured impedance UDAP Imp (meas) of any electrode has exceeded the Imp (max). If no MAP of anyone or more electrodes has violated any UDAPs, the process proceeds to query 134 to determine if the ablation session time clock has exceeded UDAP Time (max). If Time(max) has been exceeded, the controller stops output power to all electrodes to termination the ablation session, per operation 136.

If Time (max) has not been exceeded, the process returns to operation 112 where the controller continues with the ablation session by acquiring MAPs, and determining whether any UDAPs have been violated by the MAPs, until the time clock exceeds the UDAP Time (max), per operation 124, where the process proceeds to operation 136 and terminates the ablation session by stopping output power to all electrodes.

If in query 114, the controller 20 determines that one or more MAPs of one or more electrodes have violated one or more UDAPs, the controller 20 reduces output power to the one or more violating electrodes in accordance with one or more power control curves, per operation 116.

In operation 118, the controller acquires electrode temperature, including the temperature of the violating electrode(s) whose power has been reduced. In this regard, it is understood that a reduction in output power provided to an electrode should ideally immediately result in a temperature decrease of the electrode. Accordingly, in query 120, the controller identifies any electrode whose measured temperature has decreased following a reduction in power, and in operation 122 the controller resumes output power to those electrodes only. In that regard, the present invention recognizes that an electrode that is immediately responsive to power reduction by a temperature reduction is likely indicative of an arterial wall site not prone to spasming.

In operation 124, the controller implements a power reduction count for all remaining violating electrodes whose measured temperature did not decrease following the reduction in power. In query 126, if the power reduction count has exceeded the threshold SDAP C(s-max) in that a violating electrode has had more than a predetermined number of power reductions that were not followed by a measured temperature decrease, the controller in operation 128 stops output power to those electrodes as another safety measure. In that regard, the present invention recognizes that an electrode that is unresponsive or not immediately responsive to power reduction by a temperature reduction is likely indicative of an arterial wall site that is prone to spasming.

As an additional safety measure in the present invention, the process proceeds to operation 130 where the controller determines ΔP(det) and ΔTime(det) for each electrode, and in operation 132 stops output power to only the one or more electrodes whose ΔP/ΔT exceed SDAP ΔP/ΔT(s-max). In that regard, the present invention recognizes that an electrode whose measured temperature has triggered the controller to reduce power at a rate greater than a threshold rate is likely indicative of an arterial wall site that is prone to spasming. The process then continues to query 134 to assess whether the ablation session time clock as exceeded UDAP Time(max), as described above. If so, operation 136 stops output power to all electrodes. If not, the process returns to operation 112 to acquire MAPs and proceed as described above.

Figure 8:
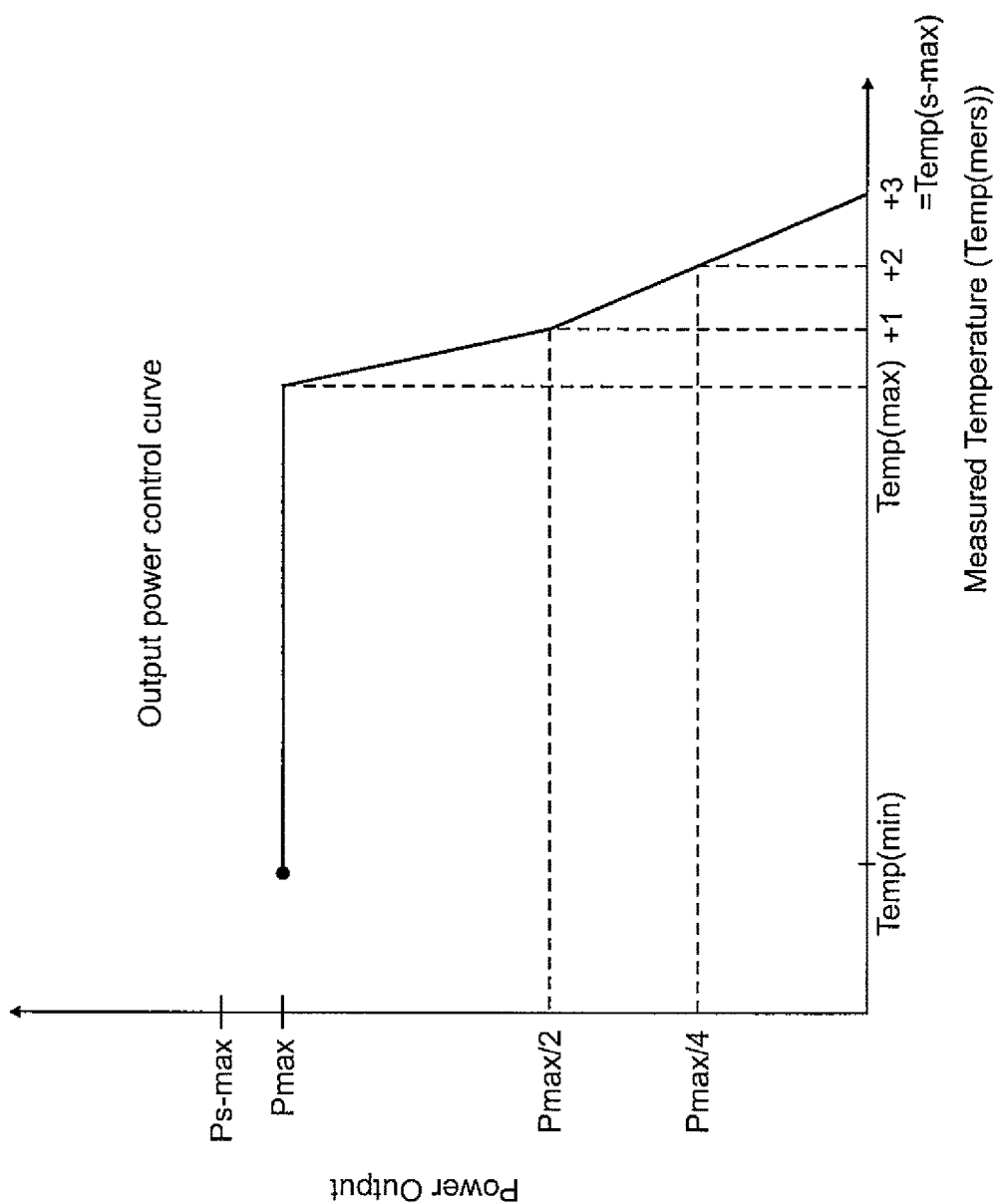
FIG. 8 is a graph illustrating example power control curve according to one embodiment of the present invention.

FIG. 8 is a graph illustrating a control curve or power control curve as a function of electrode temperature according to one embodiment of the present invention. The controller sets the output power for each electrode at the maximum value UDAP P(max) which is below SDAP P(s-max). P(max) is applied by the RF generator during the ablation session where MAP Temp(meas) ranges between UDAP Temp (min) and UDAP Temp (max). However, if MAP Temp(meas) of any electrode exceeds SDAP Temp (max) by the SDAP ΔTemp or greater, the controller reduces output power to violating electrode(s) by 50%, and continues to reduce output power by 50% for every additional increase of +1 C thereafter. If the T(meas) of any electrode increases to or at any time equals SDAP T(s-max), for example, UDAP Temp(max)+3 C, the output power to violating electrode(s) is dropped to zero or stopped.

As mentioned, the measured electrode temperature should ideally decrease immediately whenever power applied to the electrode is reduced. Thus, for one or more electrodes where the measured temperature has exceeded UDAP Temp (max), the controller responds by reducing output power to the one or more electrodes, for example, by 50%. In some embodiments, the controller responds by dropping power, for example, 3 W in one second. If the following measured temperature does not decrease, the controller responds again by reducing output power to the one or more electrodes, for example, by another 50%. The controller repeats this process of assessing measured electrode temperature and reducing output power for a predetermined plurality (for example, twice within 10 ms) within a predetermined duration of time. If the measured temperature does not decrease (or decrease sufficiently) during this process, the controller stops or zeros the output power to the one or more electrodes. In accordance with a feature of the present invention, the failure of the one or more electrodes to decrease (or decrease sufficiently) is recognized as an indicator of arterial spasm.

The controller also monitors a rate of power reduction in stopping or zeroing the output power. If the rate of power reduction exceeds a predetermined rate for one or more electrodes, the controller stops or zeros the output power to the one or more electrodes. In accordance with a feature of the present invention, the controller's reduction of output power at a rate exceeding a threshold rate is recognized as an indicator of arterial spasm.

Figure 9A:
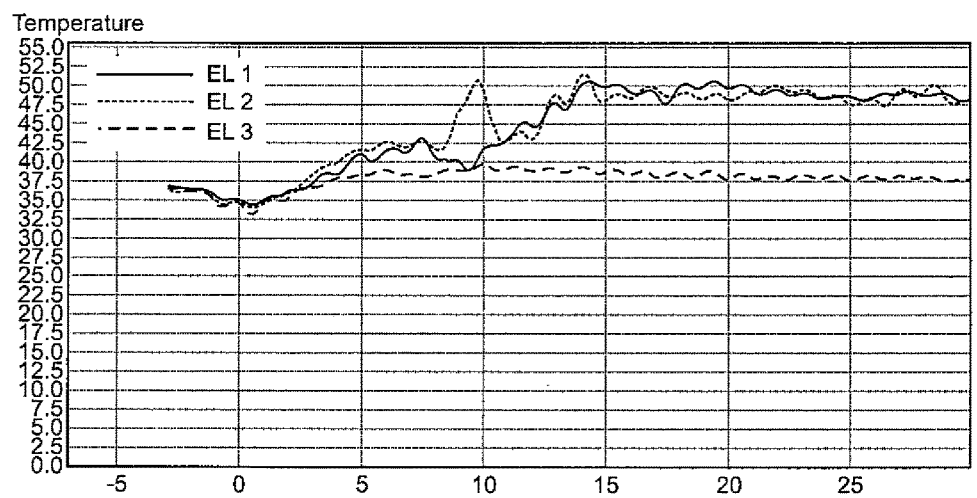
FIG. 9A is an example graph of measured temperature versus time of three electrodes of the catheter of FIG. 3.
Figure 9B:
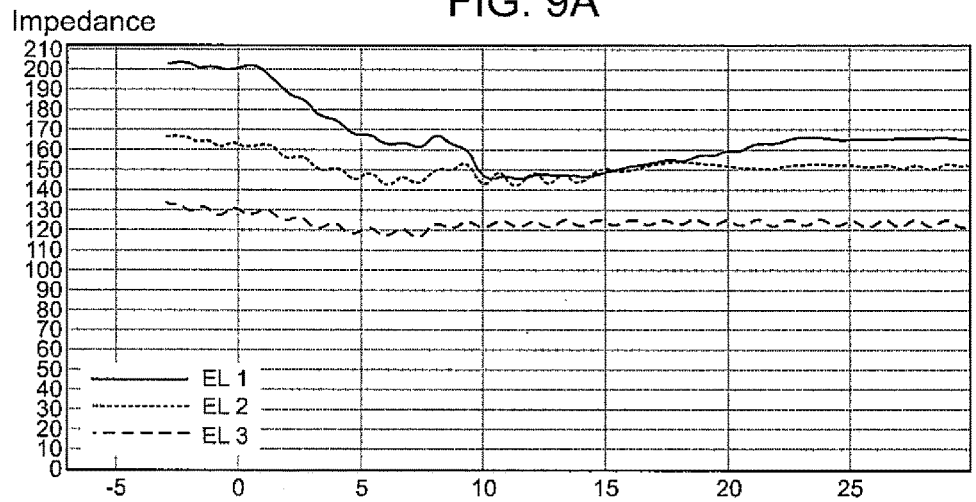
FIG. 9B is an example graph of measured impedance versus time of the three electrodes of FIG. 9A.
Figure 9C:
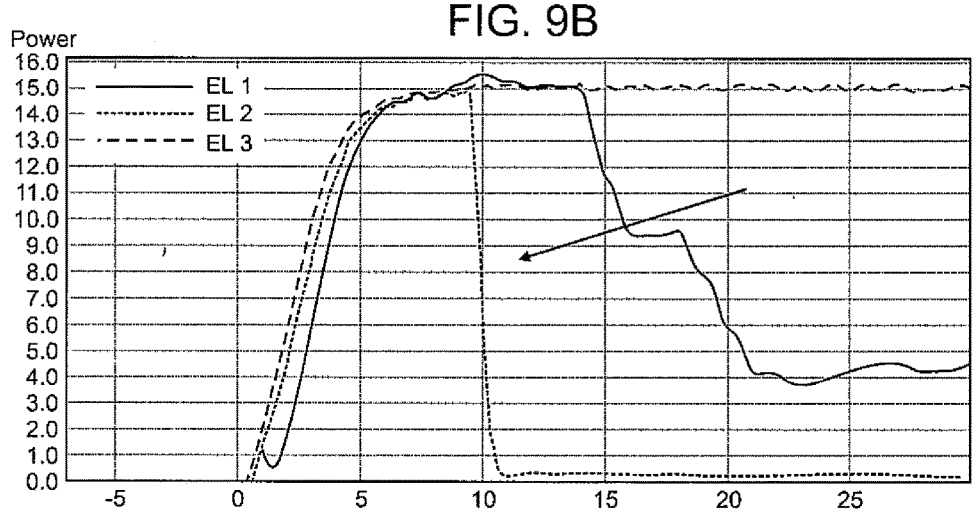
FIG. 9C is an example graph of power versus time of the three electrodes of FIG. 9A.

FIG. 9A, FIG. 9B and FIG. 9C are graphs illustrating temperature-over-time, impedance-over-time and output power-over-time activities of three electrodes EL1, EL2, and EL3 during an ablation session with Time(max) of 30 seconds, P(max) of 15 W and Temp(max) of 50 C. In FIG. 9A, the measured temperatures of electrodes EL1 and EL2 show comparable ranges between about 35 C-52 C and track each other closely except for the local peak of electrode EL2 at 10 seconds into the ablation session. The measured temperature of electrode EL3 shows a smaller range between about 33.5 C-40 C, with the least variations throughout the ablation session.

In FIG. 9B, the measured impedances of all three electrodes EL1, EL2 and EL3 show a general decrease throughout the ablation session. Electrodes EL2 and EL3 track each other closely except that the measured impedance of electrode EL2 is about 30Ω higher than the electrode EL1 throughout the ablation session. The measured impedance of electrode EL1 shows the greatest decrease from a maximum 200Ω at 0 seconds, to a minimum of about 145Ω at 10 seconds, and then a slight increase to about 165Ω at 25 seconds.

Output power adjustments by the controller in response to various ablation parameters, including the measured temperature and measured impedance of electrodes EL1, EL2 and EL3, in accordance with one embodiment of the present invention are shown in FIG. 9C. The controller applies similar output power to each of the three electrodes with a rise at a generally linear rate in output power from 0.0 W at 0 seconds to 13 W at 9 seconds. At 10 seconds into the ablation session, the output power to electrodes EL1 and EL2 is maintained at 15 W but the output power to electrode EL2 is reduced significantly by about 75% from 15 W to 3.5 W in about 1.0 second. This significant output power reduction is implemented by the controller in response to the sharp increase in the measured temperature of electrode EL2 from 42.0 C at 8 seconds into the ablation session to 51 C at 9.5 seconds, as shown in FIG. 9A. Notably, the measured temperature of 51 C exceeds the Temp(max). Advantageously, the significant output power reduction of greater than 60% in less than 1 second implemented by the controller is further recognized by the controller as an indicator of the start of a renal spasm. Accordingly, the controller ceases output power to electrode EL2 for the remainder of the ablation session.

In contrast, FIG. 9C also shows that the controller implements a significant output power reduction to electrode EL1 from 15 W to 9 W between 14 and 16 seconds into the ablation session. However, because the output power reduction of 40% over two seconds is not recognized by the controller as an indicator of the start of a renal spasm, the controllers does not cease output power to electrode EL1 for the remainder of the ablation session, but continues to provide output power to electrode EL1 at a reduced level. When the measured temperature of electrode EL1 drops back to below Temp(max) at 20 seconds into the ablation session, the controller increases the output power to electrode EL1.

Accordingly, the controller acquires and monitors a rate of reduction of output power ΔP/ΔTime against at least one SDAP, e.g., ΔP/ΔT(s-max), which as Table 2 lists shows, for example, at 6 W per second.

Embodiments of the present invention may also monitor a rate of change of temperature ΔTemp/ΔTime, and/or a rate of change of impedance ΔImp/ΔTime against one or more SDAPs, including ΔTemp/ΔTime(s-max) and ΔImp/ΔTime(s-max), to control, adjust, reduce and/or cease output power to one or more violating electrodes.

Embodiments of the present invention are not limited to RF signal generators and the ablation power supply may take the form of, for example, an ultrasound ablation power source, laser energy source, or cryo ablation energy source.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention. In that regard, the drawings are not necessarily to scale. Accordingly, the foregoing description should not be read as pertaining only to the precise structures described and illustrated in the accompanying drawings, but rather should be read consistent with and as support to the following claims which are to have their fullest and fair scope.

What is claimed is:

1. A renal ablation system, comprising:
a catheter comprising one or more electrodes and a detection circuitry configured to detect an ablation parameter for each electrode;
a controller coupled to the catheter, the controller comprising a processing unit and a memory storing instructions that, when executed by the processing unit, cause the processing unit to:
receive the detected ablation parameter for each electrode from the detection circuitry;
control a power supplied to at least one electrode to have a reduced power when the respective detected ablation parameter violates a defined ablation parameter;
detect a rate of power reduction for the at least one electrode; and
stop the power supplied to the at least one electrode when a respective detected rate of power reduction exceeds a threshold rate of power reduction.

2. The renal ablation system of claim 1, wherein the detected ablation parameter is selected from the group consisting of temperature and impedance.

3. The renal ablation system of claim 1, wherein the defined ablation parameter includes a system-defined ablation parameter.

4. The renal ablation system of claim 1, wherein the defined ablation parameter includes a user-defined ablation parameter.

5. The renal ablation system of claim 1, wherein the memory further stores instructions that, when executed by the processing unit, cause the processing unit to control the power supplied to the at least one electrode in accordance with a power control curve.

6. The renal ablation system of claim 5, wherein the power control curve includes a piecewise continuous function.

7. The renal ablation system of claim 1, wherein the memory further stores instructions that, when executed by the processing unit, cause the processing unit to stop the power supplied to each electrode when an ablation session time exceeds a threshold ablation session time.

8. The renal ablation system of claim 1, wherein the defined ablation parameter includes a user-defined ablation parameter, wherein the memory further stores instructions that, when executed by the processing unit, cause the processing unit to reject the user-defined ablation parameter when the user-defined ablation parameter violates a system-defined ablation parameter.

9. The renal ablation system of claim 8, wherein the user-defined ablation parameter is selected from the group consisting of maximum threshold temperature, and minimum threshold temperature, and the system-defined ablation parameter is selected from the group consisting of maximum system temperature, and threshold increase of detected temperature above the maximum threshold temperature at which the power to the at least one electrode is reduced.

10. The renal ablation system of claim 8, wherein the user-defined ablation parameter is selected from the group consisting of maximum threshold impedance, and minimum threshold impedance, and the system-defined ablation parameter is selected from the group consisting of maximum system impedance and minimum system impedance.

11. A renal ablation system, comprising:
a catheter comprising one or more electrodes and a temperature sensing circuity configured to sense a temperature for each electrode;
a controller coupled to the catheter, the controller comprising a processing unit and a memory storing instructions that, when executed by the processing unit, cause the processing unit to:
receive a detected temperature for each electrode from the temperature sensing circuitry;
control a power supplied to at least one electrode to have a reduced power level when the detected temperature of the at least one electrode is greater than a threshold temperature;
receive a detected rate of power reduction of the at least one electrode; and
stop the power supplied to at least one electrode when the detected rate of power reduction of the at least one electrode exceeds a threshold rate of power reduction.

* * * * *